(12) United States Patent
Rogers et al.

(10) Patent No.: US 7,707,087 B1
(45) Date of Patent: Apr. 27, 2010

(54) PRESENTING DATA-DRIVEN HEALTH CARE COST-SAVING OPPORTUNITIES TO HEALTH CARE CONSUMERS

(75) Inventors: Lisa H. Rogers, Palo Alto, CA (US); Adam C. Lee, Burlingame, CA (US); Patricia Keaney, Greenbrae, CA (US); Marilyn Hollinger, Millbrae, CA (US); Hetal A. Soni, Menlo Park, CA (US); Matthew J. Homier, San Francisco, CA (US)

(73) Assignee: Intuit Inc., Mountain View, CA (US)

( * ) Notice: Subject to any disclaimer, the term of this patent is extended or adjusted under 35 U.S.C. 154(b) by 87 days.

(21) Appl. No.: 12/023,745

(22) Filed: Jan. 31, 2008

(51) Int. Cl.
*G06Q 40/00* (2006.01)
(52) U.S. Cl. .................................. 705/35; 705/4
(58) Field of Classification Search ............. 705/10–44
See application file for complete search history.

(56) References Cited

U.S. PATENT DOCUMENTS

| | | | | |
|---|---|---|---|---|
| 4,491,725 A * | 1/1985 | Pritchard | ...................... | 705/2 |
| 6,385,589 B1 * | 5/2002 | Trusheim et al. | ............... | 705/2 |
| 6,484,144 B2 * | 11/2002 | Martin et al. | .................. | 705/2 |
| 6,735,569 B1 * | 5/2004 | Wizig | ............................ | 705/4 |
| 7,383,197 B1 * | 6/2008 | Neuman | ........................ | 705/3 |
| 7,392,201 B1 * | 6/2008 | Binns et al. | ..................... | 705/4 |
| 2007/0043595 A1 * | 2/2007 | Pederson | ....................... | 705/2 |
| 2008/0103815 A1 * | 5/2008 | Beg | .............................. | 705/2 |

* cited by examiner

*Primary Examiner*—Frantzy Poinvil
(74) *Attorney, Agent, or Firm*—Osha • Liang LLP (57) ABSTRACT

A method for presenting health care cost-saving opportunities to a health care consumer, the method including obtaining health care data and financial data associated with the health care consumer, identifying a plurality of health care cost-saving opportunities for the healthcare consumer using the health care data and the financial data, and presenting the plurality of health care cost-saving opportunities to the health care consumer in a user interface (UI).

25 Claims, 4 Drawing Sheets

PRESENTING DATA-DRIVEN HEALTH CARE COST-SAVING OPPORTUNITIES TO HEALTH CARE CONSUMERS

BACKGROUND

Health care consumers typically want to manage health care costs and to take advantage of available opportunities for reducing the cost of health care. Furthermore, many different opportunities for reducing health care costs exist, such as using a savings plan (e.g., a health savings account or a flexible spending account) to pay health care costs with pre-tax dollars, choosing a more cost effective health plan from options offered by an employer, choosing to use in-network health care providers rather than out-of-network health care providers, choosing a less expensive pharmacy, etc. However, health care consumers are often unaware of many opportunities to reduce health care costs that may be available and/or may not understand the financial impact of the opportunities of which they are aware. As a result, health care consumers often miss opportunities for cost savings when making health care decisions.

SUMMARY

In general, in one aspect, the invention relates to a method for presenting health care cost-saving opportunities to a health care consumer including obtaining health care data and financial data associated with the health care consumer, identifying a plurality of health care cost-saving opportunities for the healthcare consumer using the health care data and the financial data, and presenting the plurality of health care cost-saving opportunities to the health care consumer in a user interface (UI).

In general, in one aspect, the invention relates to a system for presenting health care cost-saving opportunities to a health care consumer that includes a user interface (UI) and a health care cost-saving analysis engine associated with the UI. The health care cost-saving analysis engine is configured to obtain health care data and financial data associated with the health care consumer, identify a plurality of health care cost-saving opportunities for the healthcare consumer using the health care data and the financial data, and present the plurality of health care cost-saving opportunities to the health care consumer in a user interface (UI).

In general, in one aspect, the invention relates to a user interface (UI) presenting health care cost-saving opportunities to a health care consumer, the UI including a display window that includes a first summary of a first health care cost-saving opportunity identified for the health care consumer, and a second summary of a second health care cost-saving opportunity identified for the health care consumer, wherein the first health care cost-saving opportunity and the second health care cost-saving opportunity are identified using health care data and financial data associated with the health care consumer, and wherein the first summary and the second summary comprise a cost saving for the health care consumer.

In general, in one aspect, the invention relates to a computer readable medium including executable instructions to obtain health care data associated with a health care consumer, obtain financial data associated with the health care consumer, identify a plurality of health care cost-saving opportunities using the health care data and the financial data, and present the plurality of health care cost saving opportunities to the health care consumer in a user interface (UI).

Other aspects of the invention will be apparent from the following description and the appended claims.

DETAILED DESCRIPTION

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention provide a method and system for presenting health care cost-saving opportunities to a health care consumer. A health care consumer, as used herein, includes anyone that consumes health care services directly (e.g., a health plan subscriber, a patient, an employee, or other direct consumer of health care services) or indirectly (e.g., the spouse, guardian, or parent of a health plan subscriber, a patient, an employee, or other indirect consumer of health care services). In one or more embodiments of the invention, health care data associated with the health care consumer is obtained from one or more health care data sources and financial data associated with the health care consumer is obtained from one or more financial sources. In some embodiments of the invention, some of the health care data and/or financial data may also be obtained from the health care consumer. The health care data and the financial data are then analyzed to identify health care cost-saving opportunities for the health care consumer. The identified health care cost-saving opportunities are then presented to the health care consumer using a user interface, such as a graphical user interface (GUI), a text-based display, an audio presentation system, a mobile phone screen, a pager display, or other interface. In one or more embodiments of the invention, one or more user interface commands are associated with each of the health care cost-saving opportunities displayed in the user interface. These user interface commands allow the health care consumer to access additional information about a particular health care cost-saving opportunity and/or to access web sites where the health care consumer may make changes needed to take advantage of the health care cost-saving opportunity.

In one or more embodiments of the invention, a health care cost-saving opportunity is an option for saving money on health care costs that may be available to a health care consumer. For example, options for saving money on health care that may be available to a health care consumer include, but are not limited to, using a savings plan (e.g., a flexible spending account (FSA) or a health savings account (HSA)) or increasing the amount of money deposited in a savings plan, changing health plans, buying prescription medications online, using health care providers that are in the network of the health care consumer's health plan, using generic medications instead of brand name medications, substituting an equivalent over-the-counter medications for prescription medications, "pill-splitting" (e.g., cutting a less-expensive large dose pill in half instead of taking two more expensive small-dose pills), and/or buying prescription medications from a different pharmacy. In one or more embodiments of the invention, as is explained below, the available health care data and financial data for the health care consumer for some specified period of time are analyzed to determine what cost-saving options are available to the health care consumer and how much money the health care consumer could have saved over the specified period of time had the health care consumer taken advantage of the cost-saving option. The health care cost-saving opportunities identified from the analysis are then presented to the health care consumer.

Figure 1:
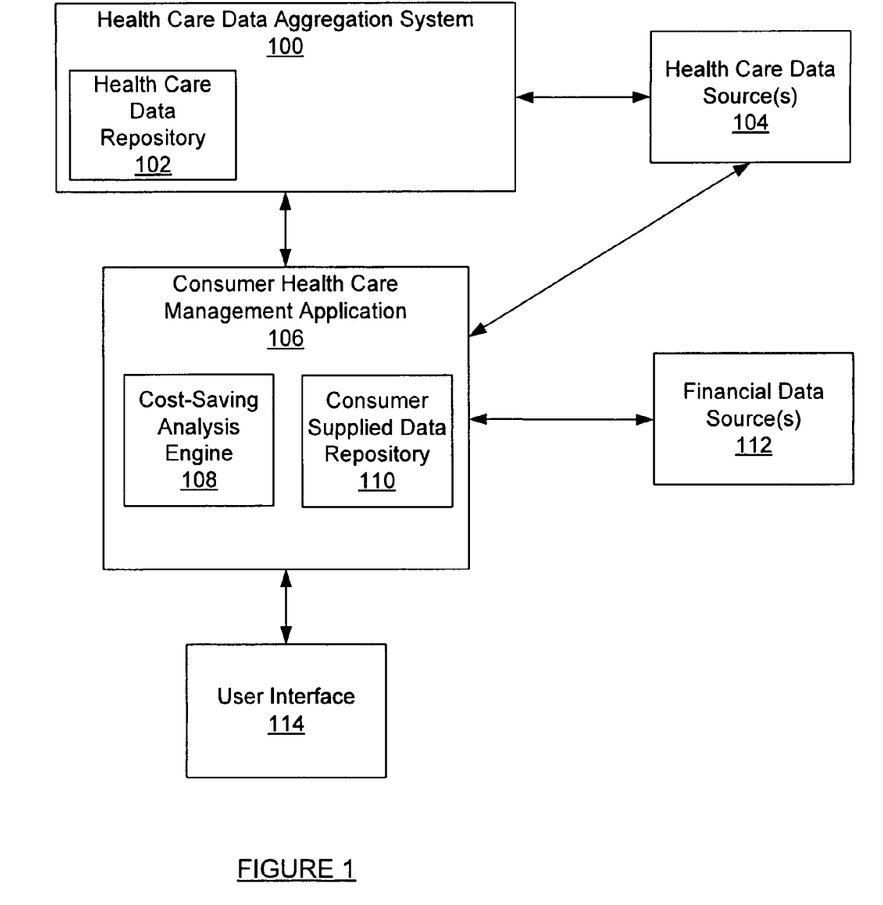
FIG. 1 shows a diagram of a system in accordance with one or more embodiments of the invention.

FIG. 1 shows a diagram of a system for presenting health care cost-saving opportunities to a health care consumer in accordance with one or more embodiments of the invention. The system includes a health care data aggregation system (100), a consumer health care management application (106), health care data source(s) (104), financial data source(s) 112, and a user interface (114). In one or more embodiments of the invention, components of the system communicate with each other via a network (e.g., a wide area network (WAN) such as the Internet, a wireless network, a local area network (LAN), or a combination of networks). Furthermore, although health care data source(s) (104) and financial data sources(s) (112) are presented and described herein as distinct sources of, respectively, health care data and financial data, one of ordinary skill in the art will understand that in one or more embodiments of the invention, some health care data and some financial data as described herein may be the same, and accordingly, some financial data sources as described herein may be also be health care data sources as described herein, and vice versa.

The health care data source(s) (104) are sources of health care data for a health plan consumer. A health care data source may be, for example, a health plan provider such as Aetna, United Healthcare, Humana, etc., a financial institution, a health care provider such as a physician, dentist, pharmacist, hospital, or laboratory, an employer, or any other source of health care data. In one or more embodiments of the invention, one or more of the health care data source(s) (104) are configured to allow the health care data aggregation system (100) with proper authentication if needed, to download, import, or otherwise access health care data corresponding to one or more health care consumers. For example, if a health care data source is a health plan provider, the health care data aggregation system (100) may download health care data associated with one or more members of health plans provided by the health plan provider.

In one or more embodiments of the invention, one or more of the health care data source(s) (104) are configured to allow the consumer health care management application (106), with proper authentication (if needed), to download, import, or otherwise access health care data corresponding to a health care consumer using the consumer health care management application (106). For example, if a health care data source is a service providing management of FSA accounts for an employer of the health care consumer, the consumer health care management application (106) may download health care data from the service related to the use of the FSA account by the health care consumer (e.g., amounts deposited and amounts withdrawn).

In one or more embodiments of the invention, health care data may include health claim data from benefit claims (e.g., medical claims, dental claims, pharmacy claims, vision claims, etc.) submitted by or on behalf of members (i.e., health plan consumers who are covered under a health plan offered by the health plan provider) to one or more benefit plans included in a health plan provided by the health plan provider. The health claim data may include data describing health plan claims, such as the claim number, the date of service, the health care service provider's name and/or contact data, the insured party's name and/or contact data, the date the insurance claim was processed by the health plan provider, the type of service(s) provided, the amount billed for each health care service, the amount allowed by the health plan, the amount paid by the health plan provider, the insured party's financial responsibility, any other type of data associated with health plan claims, or any combination thereof.

Health care data may also include, but is not limited to, information about the costs and coverage of various health plans and benefit plans offered by a health plan provider, information about physicians and other health care providers (e.g., hospitals, laboratories, therapists, etc.) included in the network of a health plan provider, information about the costs and coverage of various health plans and benefit plans offered by an employer of a health care consumer, information about the costs of prescription medications available from different sources (e.g., online pharmacies and/or a specific brick and mortar pharmacies), and information about actual use of an FSA and/or HSA.

The financial data source(s) (112) are sources of financial data for a health plan consumer. A financial data source (112) may be, for example, a financial institution, an employer, a financial management application (for personal and/or business use), an electronic tax return from a tax preparation application, an employer, or any other source of financial data relevant to identifying a health care cost saving opportunity for a health care consumer. In one or more embodiments of the invention, financial data for a health plan consumer includes, but is not limited to, gross income, income taxes paid, amounts paid for health insurance, and amounts paid to health care providers.

In one or more embodiments of the invention, the financial data source(s) (112) are configured to allow the consumer health care management application (106), with proper authentication (if needed), to download, import, or otherwise access financial data corresponding to a health care consumer using the consumer health care management application (106). For example, if a financial data source (112) is a financial management application, the consumer health care management application (106) may import relevant financial data (e.g., amounts paid to health care service providers, amounts paid for health plan coverage, amounts deposited and/or withdrawn from an FSA or HSA, total income, etc., over a specified time period) using a data export interface provided by the financial management application.

The health care data aggregation system (100) is configured to provide health care data to the consumer health care management application (106). More specifically, the health care data aggregation system (100) is configured to receive from the consumer health care management application (106) requests related to health care data of the health care consumer that may be available from the health care data aggregation system (100) and to generate responses to those requests. The health care data aggregation (100) is further configured to import health care data associated with one or more health care consumers from each of the health care data sources (104) and to store the imported health care data in the health care data repository (102). In one or more embodiments of the invention, the health care data repository (102) may be, for example, a database, a file system, one or more data structures configured in the memory of the health care data aggregation system (100), an extensible markup language (XML) file, a text file, a spreadsheet, any other type of data repository, or a suitable combination thereof. In one or more embodiments, the health care data repository (102) is stored in a data server (not shown) communicatively coupled with the health care data aggregation system (100).

In one or more embodiments of the invention, the health care data aggregation system (100) may be a health care data access service as described in U.S. patent application Ser. No. 11/799,170 entitled "METHOD AND SYSTEM FOR HEALTHCARE DATA EXCHANGE" and incorporated herein by reference in its entirety. Further, a health care data transfer (HCDT) protocol as described in the referenced patent application may be used for communication between the health care data aggregation system (100), the health care data source(s) (104), and/or the consumer health care management application (106).

The consumer health care management application (106) includes a cost-saving analysis engine (108) and a consumer supplied data repository (110). The consumer health care management application (106) may be a hosted service (e.g., a web service or any other type of backend service), an execution thread in a stand-alone end-user application, any other type of service, or any combination thereof. Depending on the type of service used, the cost-saving analysis engine (106) may be a package, a class, a method, an executable file, any other type of service component, or any combination thereof.

The consumer supplied data repository (110) is a repository of health care and/or financial data supplied to the consumer health care management application (106) by the health care consumer. The consumer supplied data repository (110) may be a database, an extensible markup language (XML) file, a text file, a spreadsheet, any other type of data repository, or any combination thereof. In one or more embodiments, the consumer supplied data repository (110) is stored in a data server (not shown) communicatively coupled with the consumer health care management application (106). Further, the consumer supplied data repository (110) may be a portion of a larger, combined repository (not shown) that also includes the health care repository (102).

In one or more embodiments of the invention, the consumer health care management application (106) is configured to access the health care data aggregation system (100), the health care data source(s) (104), and/or the financial data source(s) to retrieve health care data and financial data needed to perform health care cost-saving analyses for the health care consumer. In one or more embodiments of the invention, the cost-saving analysis engine (108) is further configured to apply the health care cost-saving analyses to the retrieved data to identify health care cost-saving opportunities for the health care consumer. The cost-saving analysis engine (108) is also configured to provide the results of the health care cost-saving analyses to the consumer health care management application (106) for presentation to the health care consumer.

In one or more embodiments of the invention, the cost-saving analysis engine (108) is configured to perform health care cost-saving analyses related to predetermined options for cost-saving on health care. As previously mentioned, such options may include, but are not limited to, use of an FSA and/or HSA, using different sources for prescription medications, changing health plans, and using in-network service providers. A health care cost-saving analysis provides for a cost-saving option that may include requesting any health care data and financial data that is needed for the analysis and analyzing the data to determine whether the health care consumer would have saved money had the health care consumer used the cost saving option. Because the granularity and format of data available from the various data sources may vary, analyzing the data may include performing any operations needed to extract the specific information required for the analysis from the data received and optionally for converting to a proper format.

More specifically, an analysis may include requesting relevant health care data and financial data for a specific period of time (e.g., a year, a month, a quarter, or any other appropriate time range) and calculating an estimated or actual dollar amount that the health care consumer could have saved during the specific period of time if the health care consumer had used the option.

For example, if the health care cost-saving analysis is related to an option to use an FSA, the data needed to perform the analysis may include the gross income of the health care consumer for a calendar year and the health care consumer's out-of-pocket health care expenses for the same calendar year. The consumer health care management application (106) may retrieve the gross income amount from an electronic version of the health care consumer's tax return for the calendar year and may also query a financial management application used by the health care consumer to retrieve financial transactions that include out-of-pocket health care expenses for the calendar year. The cost-saving analysis engine may then use the gross income amount and amounts of out-of-pocket health care expenses in the financial transactions to calculate the amount of money, if any, that the health care consumer could have saved on income taxes had the health care consumer put a particular amount of money in an FSA.

The cost-saving analysis engine (108) may also be configured to determine if a specific option is available to the health care consumer before performing the health care cost-saving analysis related to the option. For example, if the health care consumer only has one health plan available or is not eligible to use an FSA, the cost-saving analysis engine (106) may not perform the health care cost-saving analyses related to switching health plans or using an FSA. In this example, the cost saving analysis engine (108) may determine the availability of multiple health plans and/or an FSA, for example, based on data regarding available health plans and FSAs provided by the health care consumer and/or retrieved from employers of the health care consumer and a spouse of the health care consumer. Further, in some embodiments of the invention, the determination of whether a particular option is available to the health care consumer may be performed as an initial part of the related health care cost-saving analysis.

In some embodiments of the invention, the health care consumer may select which of the predetermined options are to be considered by the cost-saving analysis engine, i.e., to select which of the available health care cost-saving analysis are to be performed. Further, in some embodiments of the invention, the health care consumer may specify a time period (e.g., a month, year, quarter, or specific date range) for the data to be considered. In one or more embodiments of the invention, a time period may be specified for each option.

In one or more embodiments of the invention, the cost-saving analysis engine (108) may also use consumer supplied data in the consumer supplied data repository (110) when applying the one or more health care-cost saving analyses. In such embodiments, the consumer health care management application (106) is also configured to request and receive the consumer supplied data from the health care consumer using the user interface (114).

In one or more embodiments of the invention, when performing a health care cost saving analysis, the cost-saving analysis engine (108) may identify that more data is needed to perform the analysis. That is, some or all of the required health care data and/or financial data is not available from the health care data source(s) (104) and the financial data source(s) (112) known to the cost-saving analysis engine (108) or from the health care data aggregation system (100). In such embodiments, the cost-saving analysis engine (108) may be configured to withhold reporting the results of the analysis if sufficient data is not available. The cost-saving analysis engine (108) may also be configured to report that insufficient data was available for the analysis such that the health care cost-saving opportunity related to the analysis is presented to the health care consumer along with an indication that insufficient data was available to complete the analysis. The consumer health care management application (106) may also be configured to request the additional data from the health care consumer using the user interface (114).

The consumer health care management application (106) is further configured to provide results from the cost-saving analysis engine (108) for display in the user interface (114). The user interface (114) may be graphical user interface, such as a web page, a window in a stand-alone end-user application, a display on a mobile device (e.g., a personal digital assistant (PDA), a cellular telephone, or any other type of mobile device), or any other type of interactive computer display. More specifically, the user interface (114) is associated with (e.g., coupled to or operatively connected to) the cost-saving analysis engine (106) and is configured to display the health care cost-saving opportunities identified by the cost-saving analysis engine (106). In one or more embodiments of the invention, the user interface (114) is configured to present a summary of each of the health care cost-saving opportunities. This summary may include an identification of the option for cost-saving (e.g., using a savings plan such as a flexible spending account), a cost saving value representing the actual or estimated amount of money that could have been saved, and/or a short textual explanation of the health care cost-saving analysis. The short textual explanation may include specific dollar amounts and the specific financial data sources and health care data sources that provided relevant health care data and financial data for the analysis.

In one or more embodiments of the invention, the user interface (114) is also configured to allow the health care consumer enter one or more user interface commands related to each health care cost-saving opportunity displayed. The user interface commands may include requesting more detailed information about the analysis performed and/or the option for cost-saving. For example, if the option for cost-saving is to use an FSA, a user interface command for selecting a link to a web page that contains explanations, diagrams, and calculators based on the health care consumer's actual spending patterns and income may be provided.

The user interface commands may also include accessing a web site that enables the health care consumer to initiate changes needed to take advantage of the health care cost-saving opportunity. For example, if the option for cost-saving is buying medications online, a user interface command for selecting a link to an online pharmacy may be provided. Or, if the option for cost-saving is to use in network health care providers, a user interface command for selecting a link to a web page for picking in network doctors may be provided.

Figure 2:
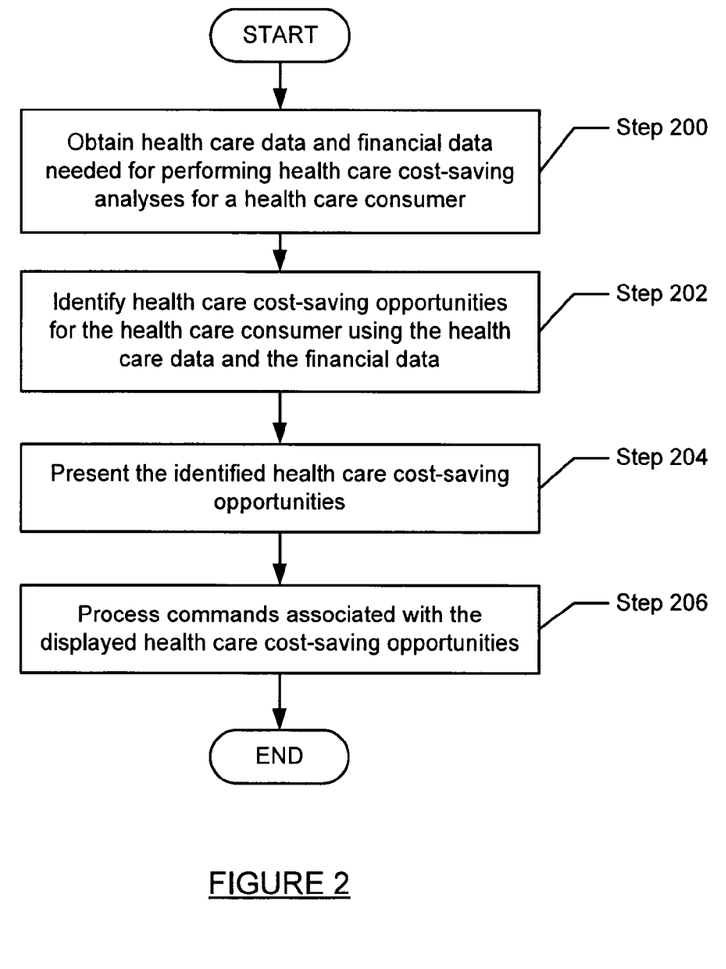
FIG. 2 shows a flowchart of a method for presenting health care cost-saving opportunities to a health care consumer in accordance with one or more embodiments of the invention.

FIG. 2 shows a flowchart of a method for presenting health care cost-saving opportunities to a health care consumer in accordance with one or more embodiments of the invention. In one or more embodiments of the invention, one or more of the steps shown in FIG. 2 may be omitted, repeated, performed in parallel, and/or performed in a different order. Accordingly, the specific arrangement of steps shown in FIG. 2 should not be construed as limiting the scope of the invention.

Initially, health care data and financial data needed for performing health care cost saving analyses for a health care consumer is obtained (Step 200) by a consumer health care management application (e.g., consumer health care management application (106) of FIG. 1) used by the health care consumer. In one or more embodiments of the invention, obtaining the financial data involves downloading, importing, or otherwise accessing the financial data from one or more financial data sources (e.g., financial data source(s) (112) of FIG. 1) storing financial data associated with the health care consumer. Further, obtaining the health care data involves downloading, importing, or otherwise accessing the health care data from a health care data aggregation system (e.g., health care data aggregation system (100) of FIG. 1). In one or more embodiments of the invention, obtaining the health care data may involve downloading, importing, or otherwise accessing the health care data from one or more health care data sources (e.g., health care data source(s) (104) of FIG. 1), which store health care data associated with the health care consumer. In one or more embodiments of the invention, some of the health care data and/or financial data may also be obtained from the health care consumer. The health care data and financial data obtained from the health care consumer may then be stored in a repository, such as the consumer supplied data repository (e.g., consumer supplied data repository (110) of FIG. 1).

Once the needed health care data and financial data are obtained, health care cost-saving opportunities for the health care consumer are identified using the obtained data (Step 202). In one or more embodiments of the invention, the identification of health care cost-saving opportunities includes performing health care cost-saving analyses related to predetermined options for cost saving on health care using the health care data and the financial data. A health care cost-saving analysis for a cost-saving option includes analyzing the data for a specific time period (e.g., a month, a quarter, a year, a specified date range, etc.) to determine how much money, if any, the health care consumer would have saved had the health care consumer used the option. In one or more embodiments of the invention, the identification is performed by a cost-saving analysis engine included in the consumer health care management application (e.g., cost-saving analysis engine (108) of FIG. 1).

For example, if the health care cost-saving analysis is related to an option to change health plans, the data obtained to perform the analysis may include the health care consumer's health care benefit claims for a calendar year downloaded from the health care consumer's health plan provider and the health care consumer's out-of-pocket costs for health insurance premiums for the same calendar year downloaded from the health care consumer's employer. The data obtained may also include the cost of insurance premiums for an alternative benefit plan offered by the employer and the costs of the health care services recorded in the benefit claims under the alternative benefit plan downloaded from the provider of the alternative benefit plan. The health care cost-saving analysis uses the actual costs incurred for health insurance premiums and the actual costs for the health care services from the benefit claims along with the premium costs and the costs for the comparable health care services under the alternative benefit plan to calculate the amount of money, if any, that the health care consumer could have saved if the health care consumer had enrolled in the alternative benefit plan.

After the health care cost-saving opportunities are identified, the opportunities are presented to the health care consumer in a user interface (e.g., user interface (114) of FIG. 1) (Step 204). In one or more embodiments of the invention, a summary of each identified health care cost-saving opportunity is displayed in the user interface. In some embodiments of the invention, one or more user interface commands related to each health care cost-saving opportunity may also be displayed. Further, user interface commands associated with the health care cost saving opportunities may be processed in response to input from the health care consumer via the user interface (Step 206). Examples of health care cost-saving opportunity (HCCSO) summaries and user interface commands are discussed below with respect to FIG. 3.

Figure 3:
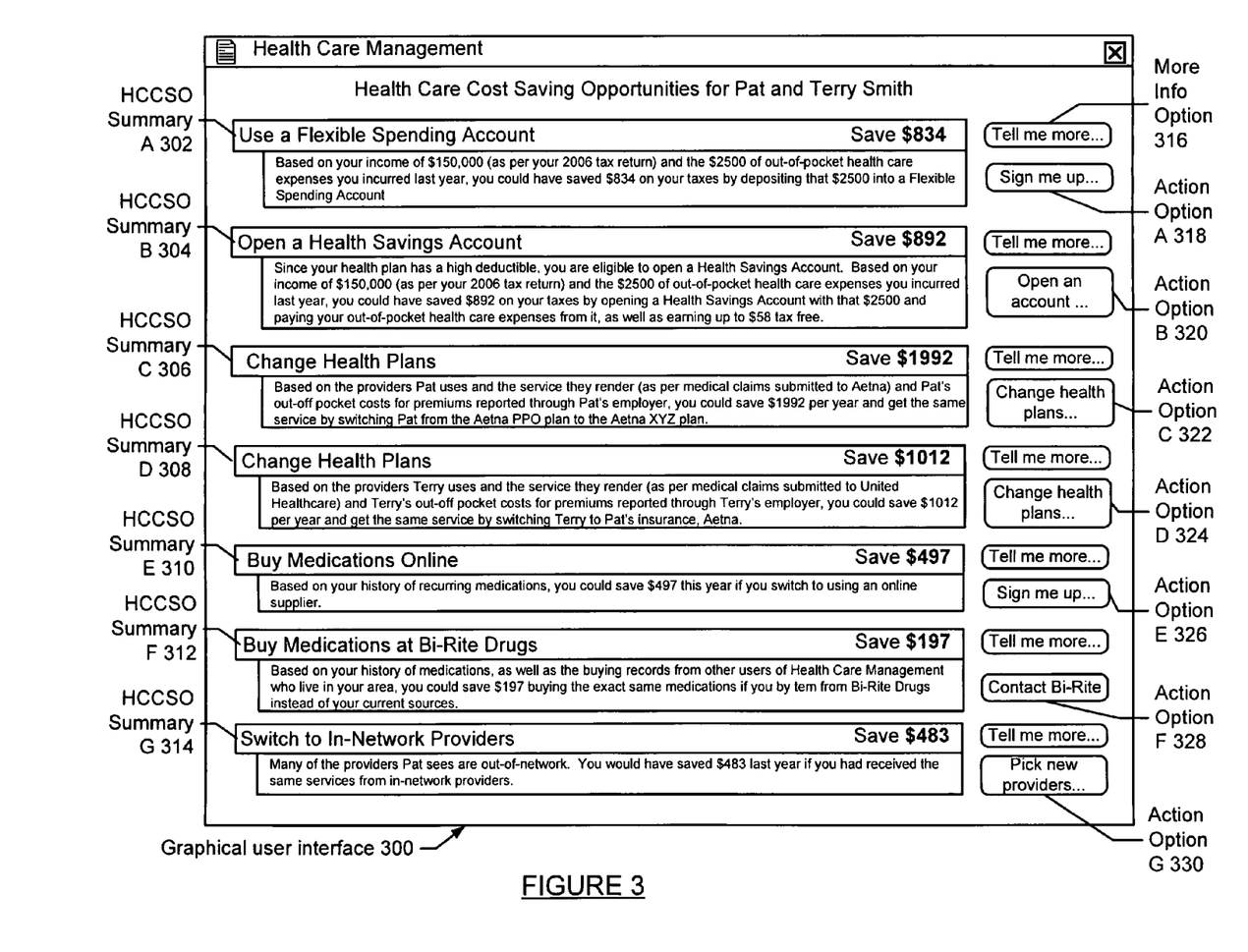
FIG. 3 shows a diagram of a graphical user interface in accordance with one or more embodiments of the invention.

FIG. 3 shows a diagram of a GUI in accordance with one or more embodiments of the invention. This GUI is provided for exemplary purposes only, and should not be construed as limiting the scope of the invention. For example, in one or more embodiments, one or more of the elements shown in FIG. 3 may have a different visual appearance or may be omitted altogether. Further, many different types of display elements and/or GUI controls may be used to implement functionality described below.

FIG. 3 shows a diagram of a GUI (300) configured to display health care cost-saving opportunities to a health care consumer. Specifically, the GUI (300) is configured to display summaries of health care cost-saving opportunities identified by analyzing health care data and financial data associated with the health care consumer, as described above. In one or more embodiments of the invention, the GUI (300) is designed to be presented directly to the health care consumer, so that the health care consumer can take appropriate actions concerning the identified health care cost saving opportunities.

In one or more embodiments of the invention, the GUI (300) includes summaries of each health care cost-saving opportunity (HCCSO) identified for the health care consumer (e.g., HCCSO Summary A (302), HCCSO Summary B (304), HCCSO Summary C (306), HCCSO Summary D (308), HCCSO Summary E (310), HCCSO Summary F (312), HCCSO Summary G (314)). Each HCCSO summary (e.g., HCCSO Summary A (302), HCCSO Summary B (304), HCCSO Summary C (306), HCCSO Summary D (308), HCCSO Summary E (310), HCCSO Summary F (312), HCCSO Summary G (314)) may include an identification of the option for cost-saving related to the HCCSO (e.g., Open a Health Savings Account in HCCSO Summary B (304)), a cost saving value representing the estimated or actual amount of money that could have been saved (e.g., Save $892 in HCCSO Summary B (304)), and a personalized short textual explanation of the health care cost-saving analysis performed to identify the HCCSO.

The textual explanation may include specific dollar amounts and the specific financial data sources that provided relevant health care data and financial data for the analysis. For example, the textual explanation of HCCSO Summary B (304) shows that the health care cost-saving analysis used a gross income amount of $150,000 from the health care consumer's 2006 tax return and an out-of-pocket health care expense amount of $2500 from the same year to calculate the amount of money the health care consumer could have saved had the health care consumer used a health savings account.

In one or more embodiments of the invention, the GUI (300) also includes links to web pages (e.g., More Info Option (316), Action Option A (318), Action Option B (320), Action Option C (322), Action Option D (324), Action Option E (326), Action Option F (328), Action Option G (330)) related to the displayed HCCSO summaries. More specifically, for each HCCSO summary displayed (e.g., HCCSO Summary A (302), HCCSO Summary B (304), HCCSO Summary C (306), HCCSO Summary D (308), HCCSO Summary E (310), HCCSO Summary F (312), HCCSO Summary G (314)), a link (e.g., More Info Option (316)) is provided to a web page that provides the health care consumer with more detailed information (e.g., explanations, diagrams, and calculators) about the related health care cost-saving analysis.

In addition, for each HCCSO summary displayed (e.g., HCCSO Summary A (302), HCCSO Summary B (304), HCCSO Summary C (306), HCCSO Summary D (308), HCCSO Summary E (310), HCCSO Summary F (312), HCCSO Summary G (314)), a link to a web page that enables the health care consumer to initiate changes needed to take advantage of the health care cost-saving opportunity is displayed (e.g., Action Option A (318), Action Option B (320), Action Option C (322), Action Option D (324), Action Option E (326), Action Option F (328), Action Option G (330)). For example, in HCCSO Summary D (308), the identified option for cost-saving is to buy medications on line. The associated link, Action Option D (324), may be a link to a web page for a specific on-line pharmacy or a link to a web page presenting a list of links to on-line pharmacies for the health care consumer to consider.

In another example, in HCCSO Summary G (314), the identified option for cost-saving is to switch to in-network providers. The associated link, Action Option G (330), may be a link to a web page that assists the health care consumer in selecting alternative in-network providers for each of the out-of-network providers previously used. In one or more embodiments of the invention, the web page may be part of a web site of a health plan provider.

In a further example, in HCCSO Summary C (306), the identified option for cost-saving is to change health plans. The associated link, Action Option C (322) may be a link a benefits web site of the health care consumer's employer where the health care consumer can chose another health plan offered by the employer. Similarly, in HCCSO Summary D (308), the identified option for cost-saving is also to change health plans. However, in this instance, the cost-saving may be achieved by switching from the health plan of the health care consumer's employer to that offered by the employer of the health care consumer's spouse. The associated link, Action Option D (324), may be a link to a web page including links to the benefits web sites of each of the employers.

In yet another example, in HCCSO Summary F (312), the identified option for cost-saving is to buy medications at a specific bricks and mortar pharmacy. The associated link, Action Option F (328), maybe a link to the web site of that pharmacy or may be a web page containing contact information (e.g., telephone number and address) for the pharmacy.

Figure 4:
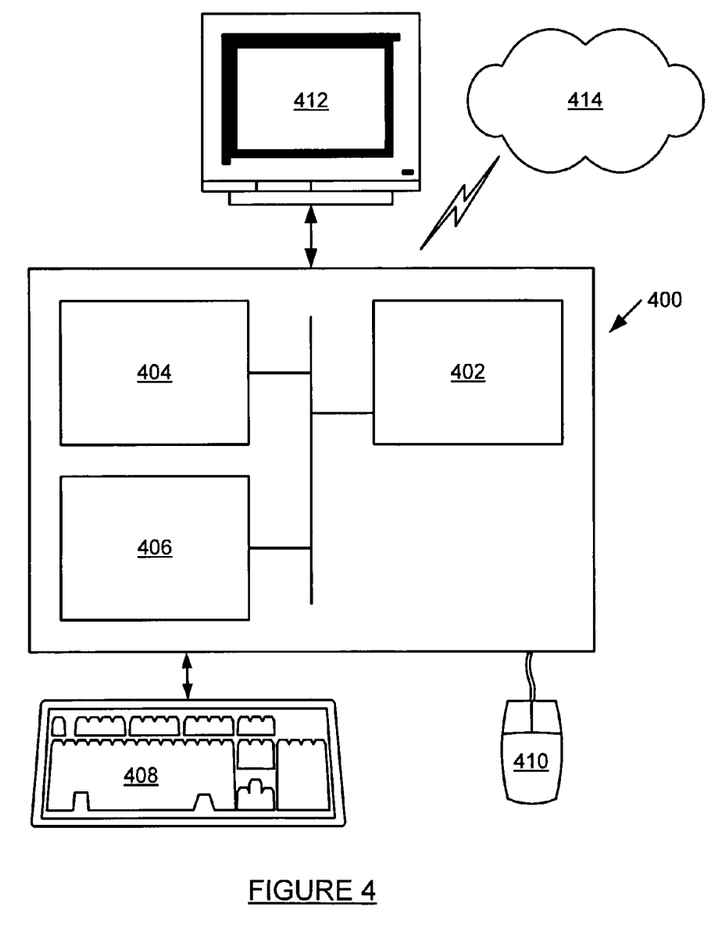
FIG. 4 shows a diagram of a computer system in accordance with one or more embodiments of the invention.

Embodiments of the invention may be implemented on virtually any type of computer regardless of the platform being used. For example, as shown in FIG. 4, a computer system (400) includes a processor (402), associated memory (404), a storage device (406), and numerous other elements and functionalities typical of today's computers (not shown). The computer (400) may also include input means, such as a keyboard (408) and a mouse (410), and output means, such as a monitor (412). The computer system (400) may be connected to a network (414) (e.g., a local area network (LAN), a wide area network (WAN) such as the Internet, or any other similar type of network) via a network interface connection (not shown). Those skilled in the art will appreciate that these input and output means may take other forms.

Further, those skilled in the art will appreciate that one or more elements of the aforementioned computer system (400) may be located at a remote location and connected to the other elements over a network. Further, embodiments of the invention may be implemented on a distributed system having a plurality of nodes, where each portion of the invention (e.g., health care data aggregation system, health care data repository, consumer health care management application, GUI, etc.) may be located on a different node within the distributed system. In one embodiment of the invention, the node may be a computer system. Alternatively, the node may be a processor with associated physical memory. The node may alternatively be a processor with shared memory and/or resources. Further, software instructions to perform embodiments of the invention may be stored on a computer readable medium such as a compact disc (CD), a diskette, a tape, a file, or any other computer readable storage device.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for presenting a plurality of health care cost-saving opportunities (HCCSOs) to a health care consumer, comprising:
   obtaining, using a processor of a computer, health care data and financial data associated with the health care consumer, wherein the health care data includes a medical history of the health care consumer over a time period, and wherein the financial data includes a plurality of medical expenses of the health care consumer within the time period;
   identifying, using the processor of the computer and the health care data, the plurality of HCCSOs for the plurality of medical expenses, wherein the plurality of HCCSOs have a plurality of costs;
   calculating, using the processor of the computer, a plurality of differences between the plurality of medical expenses and the plurality of costs; and
   presenting, using the processor of the computer, the plurality of HCCSOs and the plurality of differences to the health care consumer in a user interface (UI).

2. The method of claim 1, wherein presenting the plurality of HCCSOs further comprises:
   displaying a summary for a HCCSO of the plurality of HCCSOs.

3. The method of claim 2, wherein the summary further comprises at least one of a source of the health care data and a source of the financial data used to identify the HCCSO.

4. The method of claim 1, further comprising:
   responsive to selection of a UI command by the health care consumer, displaying an explanation of an analysis used to identify a HCCSO of the plurality of HCCSOs, wherein the UI command is associated with the HCCSO in the UI.

5. The method of claim 1, further comprising:
   responsive to selection of a UI command by the health care consumer, directing the health care consumer to at least one web page that assists the health care consumer in making a change corresponding to a HCCSO of the plurality of HCCSOs, wherein the UI command is associated with the HCCSO in the UI.

6. The method of claim 5, wherein the at least one web page is one selected from a group consisting of: a benefits web page provided by an employer of the health care consumer, a benefits web page provided by an employer of a spouse of the health care consumer, a web page of a pharmacy, a web page of a financial institution, and a web page of a health plan provider associated with the health care consumer.

7. The method of claim 1, wherein at least one of the plurality of HCCSOs is selected from a group consisting of: using a savings plan, changing health plans, buying medications online, buying medications at a specific pharmacy, using a generic prescription medication instead of a brand-name prescription medication, substituting an equivalent over-the-counter medication for a prescription medication, and changing providers.

8. The method of claim 1, wherein the health care data is obtained from at least one selected from a group consisting of: a health plan provider associated with the health care consumer, a health care services provider associated with the health care consumer, an employer associated with the health care consumer, a financial institution associated with the health care consumer, and a service that manages flexible spending accounts associated with the health care consumer.

9. The method of claim 1, wherein the financial data is obtained from at least one selected from a group consisting of: an employer associated with the health care consumer, a tax return associated with the health care consumer, a personal financial management application associated with the health care consumer, and a financial institution associated with the health care consumer.

10. A system for presenting a plurality of health care cost-saving opportunities (HCCSOs) to a health care consumer, comprising:
    a processor;
    a user interface (UI) executing on the processor; and
    a health care cost-saving analysis engine executing on the processor and associated with the UI, wherein the health care cost-saving analysis engine is configured to:
       obtain health care data and financial data associated with the health care consumer, wherein the health care data includes a medical history of the health care consumer over a time period, and wherein the financial data includes a plurality of medical expenses of the health care consumer within the time period;
    identify the plurality of HCCSOs for the plurality of medical expenses using the health care data, wherein the plurality of HCCSOs have a plurality of costs;
    calculate a plurality of differences between the plurality of medical expenses and the plurality of costs; and
    present the plurality of HCCSOs and the plurality of differences to the health care consumer in the UI.

11. The system of claim 10, wherein the health care cost-saving analysis engine is further configured to present the plurality of HCCSOs by:
    displaying a summary describing a HCCSO of the plurality of HCCSOs.

12. The system of claim 11, wherein the summary further comprises at least one of a source of the health care data and a source of the financial data used to identify the HCCSO.

13. The system of claim 10, wherein the health care cost-saving analysis engine is further configured to:
    responsive to selection of a UI command by the health car consumer, display an explanation of an analysis used to identify a HCCSO of the plurality of HCCSOs, wherein the UI command is associated with the HCCSO in the UI.

14. The system of claim 10, wherein the health care cost-saving analysis engine is further configured to:

responsive to selection of a UI command by the health care consumer, direct the health care consumer to at least one web page that assists the health care consumer in making a change corresponding to a HCCSO of the plurality of HCCSOs, wherein the UI command is associated with the HCCSO in the UI.

15. The system of claim 14, wherein the at least one web page is one selected from a group consisting of: a benefits web page provided by an employer of the health care consumer, a benefits web page provided by an employer of a spouse of the health care consumer, a web page of a pharmacy, a web page of a financial institution, and a web page of a health plan provider associated with the health care consumer.

16. The system of claim 10, wherein a HCCSO of the plurality of HCCSOs is one selected from a group consisting of: using a savings plan, changing health plans, buying medications online, buying medications at a specific pharmacy, using a generic prescription medication instead of a brand-name prescription medication, substituting an equivalent over-the-counter medication for a prescription medication, and changing providers.

17. The system of claim 10, wherein the health care data is obtained from at least one selected from a group consisting of: a health plan provider associated with the health care consumer, a health care services provider associated with the health care consumer, an employer associated with the health care consumer, a financial institution associated with the health care consumer, and a service that manages flexible spending accounts associated with the health care consumer.

18. The system of claim 10, wherein the financial data is obtained from at least one selected from a group consisting of: an employer associated with the health care consumer, a tax return associated with the health care consumer, a personal financial management application associated with the health care consumer, and a financial institution associated with the health care consumer.

19. An apparatus comprising a processor executing a user interface (UI) for presenting a plurality of health care cost-saving opportunities (HCCSOs) to a health care consumer, the UI comprising:

a display window comprising:

a first summary of a first HCCSO identified for the health care consumer; and a second summary of a second HCCSO identified for the health care consumer, wherein the first HCCSO and the second HCCSO are identified using health care data and financial data associated with the health care consumer, wherein the health care data includes a medical history of the health care consumer over a time period, and wherein the financial data includes a plurality of medical expenses of the health care consumer within the time period, wherein the first HCCSO and the second HCCSO have a plurality of costs, and wherein the first summary and the second summary comprise a plurality of calculated differences between the plurality of medical expenses and the plurality of costs.

20. The apparatus of claim 19, wherein the first summary further comprises at least one of a source of the health care data and a source of the financial data used to identify the first HCCSO.

21. The apparatus of claim 19, wherein the UI further comprises a UI command for accessing an explanation of an analysis used to identify the first HCCSO.

22. The apparatus of claim 19, wherein the UI further comprises a UI command for directing the health care consumer to at least one web page that assists the health care consumer in making a change related to the first HCCSO.

23. A computer readable medium storing instruction for presenting a plurality of health care cost-saving opportunities (HCCSOs) to a health care consumer, the instructions, when executed on a processor of a computer system, comprising functionality to:

obtain health care data associated with a health care consumer, wherein the health care data includes a medical history of the health care consumer over a time period;

obtain financial data associated with the health care consumer, wherein the financial data includes a plurality of medical expenses of the health care consumer within the time period;

identify the plurality of HCCSOs for the plurality of medical expenses using the health care data, wherein the plurality of HCCSOs have a plurality of costs;

calculate a plurality of differences between the plurality of medical expenses and the plurality of costs; and present the plurality of HCCSOs and the plurality of differences to the health care consumer in a user interface (UI).

24. The computer readable medium of claim 23, wherein the instructions to present the plurality of HCCSOs further comprise functionality to:

display a summary a HCCSO of the plurality of HCCSOs.

25. The computer readable medium of claim 24, wherein the summary further comprises at least one of a source of the health care data and a source of the financial data used to identify the HCCSO.

* * * * *